(12) United States Patent
Chang et al.

(10) Patent No.: US 10,729,450 B2
(45) Date of Patent: Aug. 4, 2020

(54) SURGICAL VESSEL CLIP APPLIER HANDLE

(71) Applicant: Taiwan Surgical Corporation, Zhubei, Hsinchu County (TW)

(72) Inventors: Kuo-Yang Chang, Zhubei (TW); Chien-Wei Sun, Zhubei (TW)

(73) Assignee: Taiwan Surgical Corporation, Zhubei (TW)

( * ) Notice: Subject to any disclaimer, the term of this patent is extended or adjusted under 35 U.S.C. 154(b) by 179 days.

(21) Appl. No.: 16/056,647

(22) Filed: Aug. 7, 2018

(65) Prior Publication Data

US 2019/0053809 A1 Feb. 21, 2019

(30) Foreign Application Priority Data

Aug. 18, 2017 (TW) .............................. 106128191 A

(51) Int. Cl.
*A61B 17/128* (2006.01)
*A61B 17/29* (2006.01)
*A61B 17/00* (2006.01)

(52) U.S. Cl.
CPC ...... *A61B 17/1285* (2013.01); *A61B 17/2909* (2013.01); *A61B 2017/0046* (2013.01); *A61B 2017/00367* (2013.01); *A61B 2017/00407* (2013.01); *A61B 2017/00477* (2013.01); *A61B 2017/00778* (2013.01); *A61B 2017/2925* (2013.01)

(58) Field of Classification Search
CPC ............ A61B 17/1285; A61B 17/2909; A61B 2017/00367; A61B 2017/00407; A61B 2017/0046; A61B 2017/00477; A61B 2017/00778; A61B 2017/2925; A61B 2017/2924; A61B 2017/2912
See application file for complete search history.

(56) References Cited

FOREIGN PATENT DOCUMENTS

TW 201642812 A 12/2016

*Primary Examiner* — Ashley L Fishback
(74) *Attorney, Agent, or Firm* — Alan D. Kamrath; Mayer & Williams PC

(57) ABSTRACT

A surgical vessel clip applier handle is provided and has a head unit capable of being flipped relative to a handle body having a front end pivotally connected to the head unit. An embedding opening is formed on the top of a barrel part of the handle body. Two slides blocks are disposed inside the barrel part at a front position and a rear position. The front part of a grip part of the handle body has a trigger having a linkage assembly disposed between the trigger and the slide blocks. The invention is capable of installing and removing conventional clamping assemblies by simply flipping the head unit; when the head unit is flipped back, the rear end of the clamping assembly will connect to the slide blocks via the embedding opening, the linkage assembly thereby drives the clamping assembly to clamp while the trigger is being pulled by a user.

10 Claims, 9 Drawing Sheets

SURGICAL VESSEL CLIP APPLIER HANDLE

FIELD OF THE INVENTION

The present invention relates to a surgical instrument structure, and more particularly to a reusable surgical vessel clip applier handle of a vessel clamping instrument.

BACKGROUND OF THE INVENTION

While performing laparoscopic surgeries, blood vessels have to be closed and sealed in order to prevent blood leakage from the incision of the surgical site. Blood vessels can be closed or sealed by using specific surgical instruments, such as a vessel clip operated with a vessel clip applier. The use of such vessel clip applier is to extend a rod-like vessel clamping assembly into the human body, and then operate the grip part of such vessel clamping assembly to actuate the clamp portion at its front end to clamp the vessel clip that is sent to the clamp portion. The blood vessel clip is then pressed against the blood vessel to close it.

In order to avoid blood contaminations, the conventional vessel clip appliers are designed as disposable instruments. For instance, in TW Patent Application No. 104118985 (Publication No. 201642812), an automatic clip applier is provided having an outer sleeve on a clamping assembly, in which the front end of the clamping assembly has a clamp portion, a clip pusher for pushing the clip ahead toward the clamp portion, and a first sleeve and a second sleeve sleeved on the rear end of the clamping assembly. The clamp portion clamps while the first sleeve moves forward. At the beginning of the forward movement of the first sleeve, the second sleeve will be moved forward together with the first sleeve. Then, while the second sleeve reaches a later position, it will no longer be moved together with the first sleeve and can be moved backward to drop in another vessel clip to the inner side of the clamp portion.

The aforementioned process of triggering the movement of the clamping assembly by the automatic clip applier is to press its grip to move the corresponding linkage unit through the first and second linking members in order to link the linkage unit of the first sleeve or the second sleeve to move. The entire automatic clip applier is discarded after each use. The linkage unit between the first and second sleeves and the grip of the clamping assembly of the aforementioned automatic clip applier is a separable structure, which means that the clamping assembly is an independent structure that can be separated from the grip. However, because the grip and the clamping assembly are designed to be fixed together in an inseparable manner, both the grip and the clamping assembly have to be discarded together each time the automatic clip applier has been used, thereby greatly increasing the cost of using that kind of automatic clip appliers.

SUMMARY OF THE INVENTION

Conventional vessel clamping devices are usually disposable due to their non-reusable structural design of the handles, the cost of surgical operations using those vessel clamping devices are relatively high. Therefore, a more economical and reusable surgical vessel clip applier handle that is capable of repeatedly installing and removing clamping assemblies is provided and includes:

a handle body, being a shell and comprising a grip part and a barrel part, wherein a top portion of the grip part is connected to the bottom side of the front end portion of the barrel part, a track receiving space is formed inside the barrel part and extends along an axial direction of the barrel part, a top side of the barrel part has an embedding opening formed along the barrel part, a front end of the track receiving space and a front end of the embedding opening are open ends, a first track and a second track are respectively formed at a front portion and a rear portion of the track receiving space inside the barrel part, both the first track and the second track are tracks extending along the axial direction of the barrel part, a trigger opening is formed at the junction of where a front end of the top portion of the grip part and the bottom side of the barrel part are connected;

a drive structure, having a first slide block and a second slide block slidably disposed on the first track and the second track, respectively, and a first slide groove and a second slide groove respectively formed on the first slide block and the second slide block, wherein the first slide groove is opened at a top portion of the first slide block, and the second slide groove is opened at a top portion of the second slide block, the first slide block has a portion protruding inwardly toward the first slide groove forming a first connecting shape, the second slide block has a portion protruding inwardly toward the second slide groove forming a second connecting shape; wherein the drive structure has a trigger, a top portion of the trigger is passed through the trigger opening, the top portion of the trigger is pivotally connected to the front end of the bottom side of the barrel part, a drive arm is formed on and extended rearward from the trigger, a linkage assembly is disposed between a free end of the trigger, and the first slide block and the second slide block, thereby a first movement and a second movement of the first slide block and the second slide block are performed while the trigger has been pulled rearward to move the first slide block and the second slide block through the linkage assembly; and a head unit, having a head portion located at a front end portion of the barrel part, and a front tube extended from a center portion of the head portion toward the front, wherein a front channel is formed inside the front tube and the head portion, the front channel is communicated with the track receiving space, the periphery of the rear end of the front channel is expanded radially to form a fixing portion, a bottom side of the head portion has a pivot portion extended downwardly therefrom for pivotally connecting to the front end of the bottom side of the barrel part, a top side of the head portion is extended rearward to form an upper cover for closing the embedding opening, a switch structure is disposed between the periphery of the embedding opening and the upper cover.

While operating the present invention, the switch structure of the head unit will be switched to an open status, and then the head unit will be flipped frontward away from the barrel part in order to expose the embedding opening. At this moment, the clamping assembly can be installed by inserting the clamping assembly downwardly into the front channel of the head unit. Afterward, the head unit will be flipped back to its original position, and the embedding opening will be covered by the upper cover. Finally, the switch structure will be switched to a close status where the upper cover is fixed to the embedding opening. While the rear end of the clamping assembly is inserted into the barrel part through the embedding opening, the first sleeve and the second sleeve of the rear end of the clamping assembly will be respectively embedded into the first groove of the first slide block and the second groove of the second slide block, so that the movement of the first connecting shape of the first slide block can be linked with the first sleeve, and the movement of the second connecting shape of the second slide block can be linked with the second sleeve.

When pulling the trigger, the linkage assembly will drive the first slide block and the second slide block to perform the first movement and the second movement, respectively. The first slide block and the second slide block move the first sleeve and the second sleeve of the clamping assembly for driving the clamping portion at the front end of the clamping assembly to clamp the vessel clip being sent frontward. While the operation of the clamping assembly is done, the switch structure will be switched to the open status to flip up the head unit in order to remove the used clamping assembly, and then a new one can be installed for further operations after sterilizing the surgical vessel clip applier handle of the present invention.

The clamping assembly can be repeatedly installed and removed by operating with the present invention, and only the used clamping assembly is to be discarded after each operation, thereby being more economical and saving the cost of the use of vessel clamps. In addition, the use of the present invention can reduce the risk of infection by easily replacing the clamping assembly that has direct contact with the human body with a new one after each use. Furthermore, during installation, the long rod-like clamping assembly is inserted along a downward direction into the head unit while the head unit is flipped up, as a result, the operation space required for the installation process is relatively small and the installation position and process are more ergonomic, and thereby being easier to use.

BRIEF DESCRIPTION OF THE DRAWINGS

The structure and the technical means adopted by the present invention to achieve the above and other objects can be best understood by referring to the following detailed description of the preferred embodiments and the accompanying drawings.

DETAILED DESCRIPTION OF THE PREFERRED EMBODIMENTS

Figure 1:
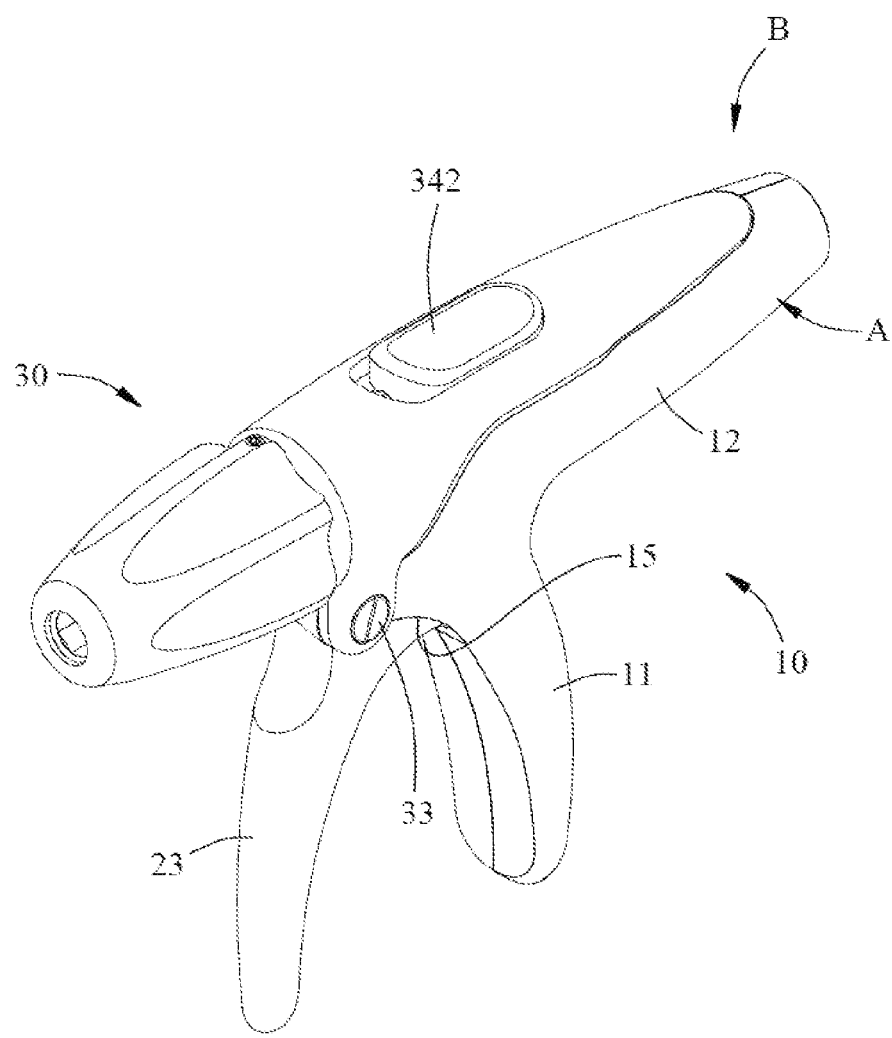
FIG. 1 is a perspective view of a preferred embodiment of the present invention.

Reference will now be made in detail to the presently preferred embodiments of the invention, examples of which are illustrated in the accompanying drawings. Wherever possible, the same reference numbers are used in the drawings and the description to refer to the same or like parts. It is not intended to limit the method or the system by the exemplary embodiments described herein. In the following detailed description, for purposes of explanation, numerous specific details are set forth in order to attain a thorough understanding of the disclosed embodiments. It will be apparent, however, that one or more embodiments may be practiced without these specific details. As used in the description herein and throughout the claims that follow, the meaning of "a", "an", and "the" includes reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to. As used in the description herein and throughout the claims that follow, the meaning of "in" includes "in" and "on" unless the context clearly dictates otherwise.

It will be understood that when an element is referred to as being "connected" to another element, it can be directly connected to the other element or intervening elements may be present.

Figure 2:
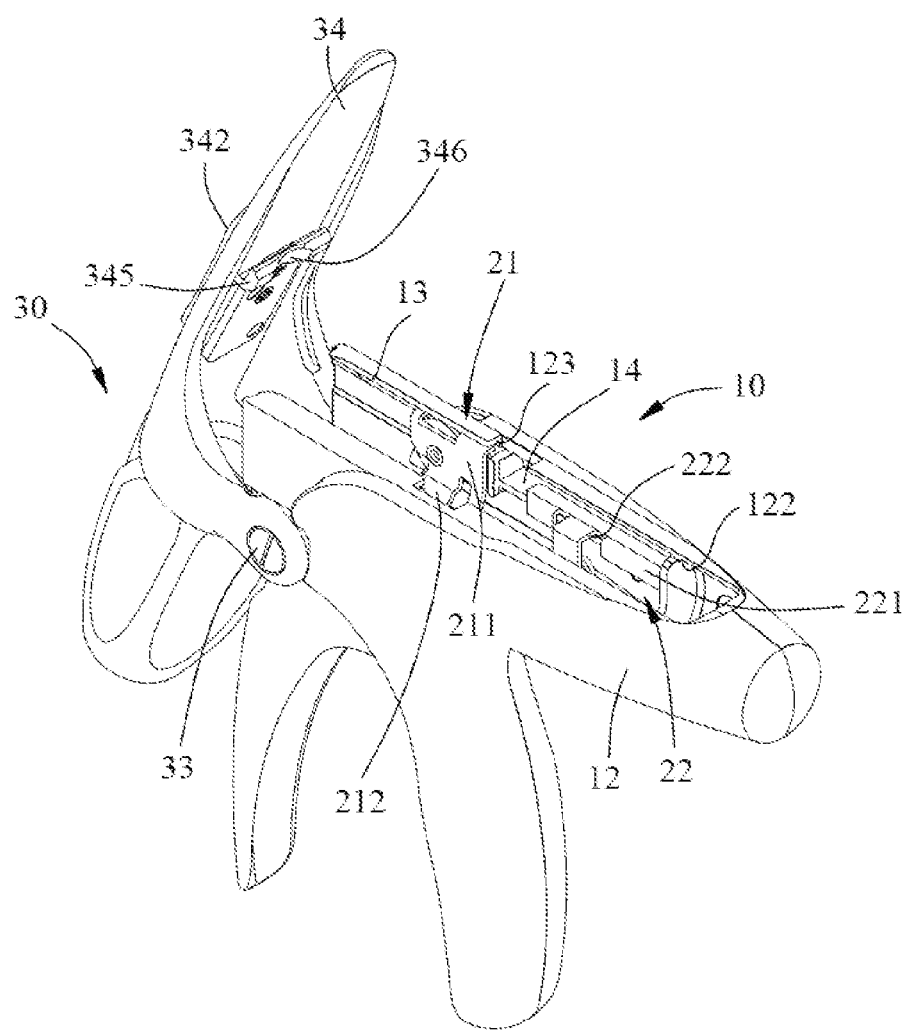
FIG. 2 is a perspective view illustrating a head unit in an open status according to a preferred embodiment of the present invention.
Figure 3:
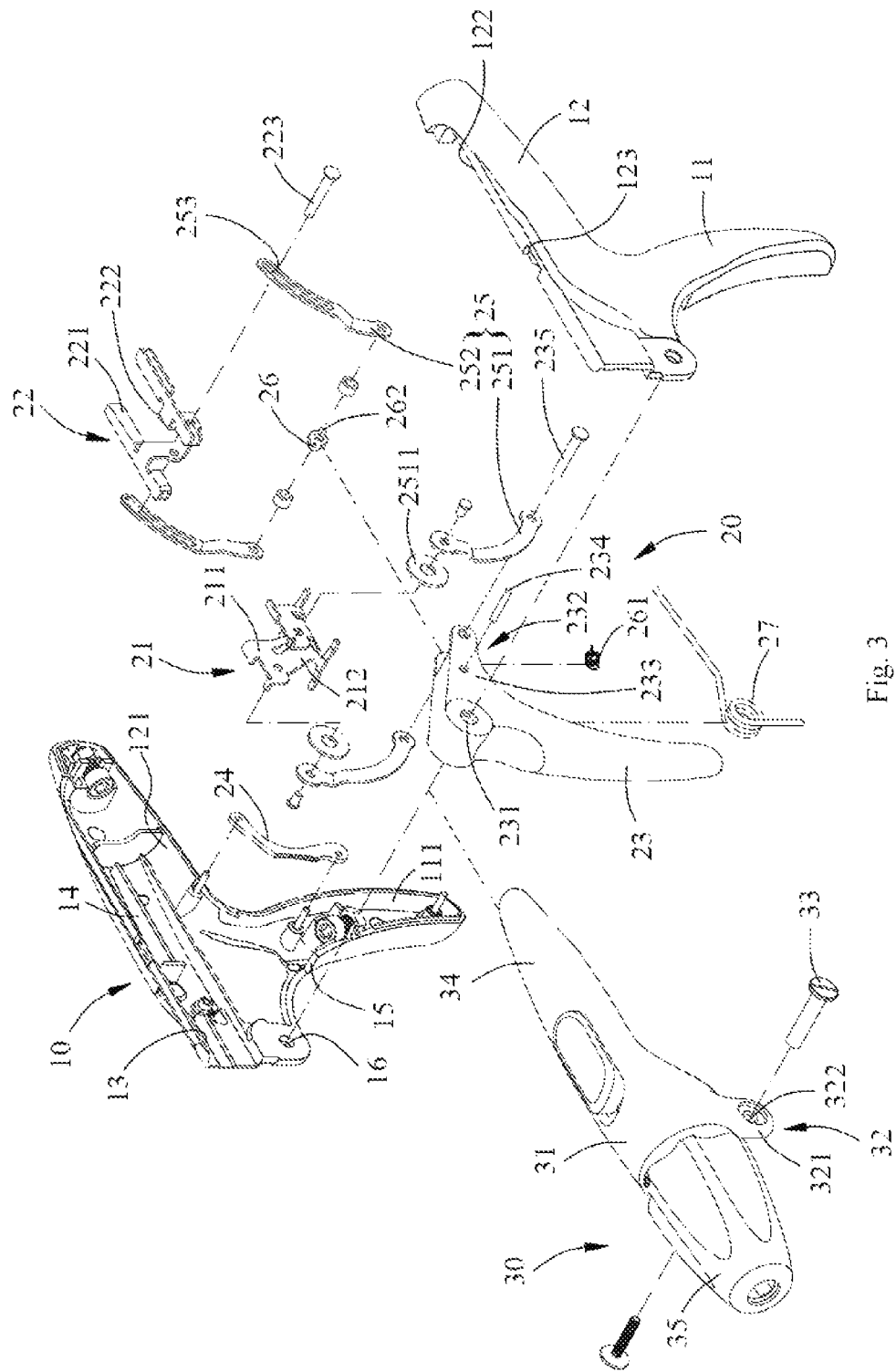
FIG. 3 is an explosion view of a preferred embodiment of the present invention.

Referring to preferred embodiments of the present invention shown in FIG. 1 to FIG. 5, a surgical vessel clip applier handle is provided and includes a handle body 10, a drive structure 20 disposed in the handle body 10, and a head unit 30 pivotally connected to the front end of the handle body 10, in which:

With reference to FIG. 1 to FIG. 3, the handle body 10 includes a left handle shell A and a right handle shell B, the handle body 10 is literally a housing formed by combining the left handle shell A and the right handle shell B. The handle body 10 includes a grip part 11 and a barrel part 12. A top portion of the grip part 11 is connected to a bottom side of a front end portion of the barrel part 12, an accommodation space 111 is formed inside the grip part 11, the barrel part 12 is a housing extended in a front-to-rear direction, a track receiving space 121 is formed inside the barrel part 12 and extends along the axial direction of the barrel part 12, the track receiving space 121 is communicated with the accommodation space 111, the top side of the barrel part 12 has an embedding opening 122 formed along the barrel part 12, an aperture 123 is formed at the opposite sides of the peripheral edge of the embedding opening 122, each of the track receiving space 121 and the embedding opening 122 has a front end being an open end, a first track 13 and a second track 14 are respectively formed at a front portion and a rear portion of the track receiving space 121 inside the barrel part 12, both the first track 13 and the second track 14 are tracks extending along the axial direction of the barrel part 12, a trigger opening 15 is formed at the junction where a front end of the top portion of the grip part 11 and the bottom side of the barrel part 12 are connected. A barrel part shaft hole 16 is formed laterally at the front edge of the bottom part of the barrel part 12, and more specifically, the barrel part shaft hole 16 is penetrated through the barrel part 12.

Figure 5:
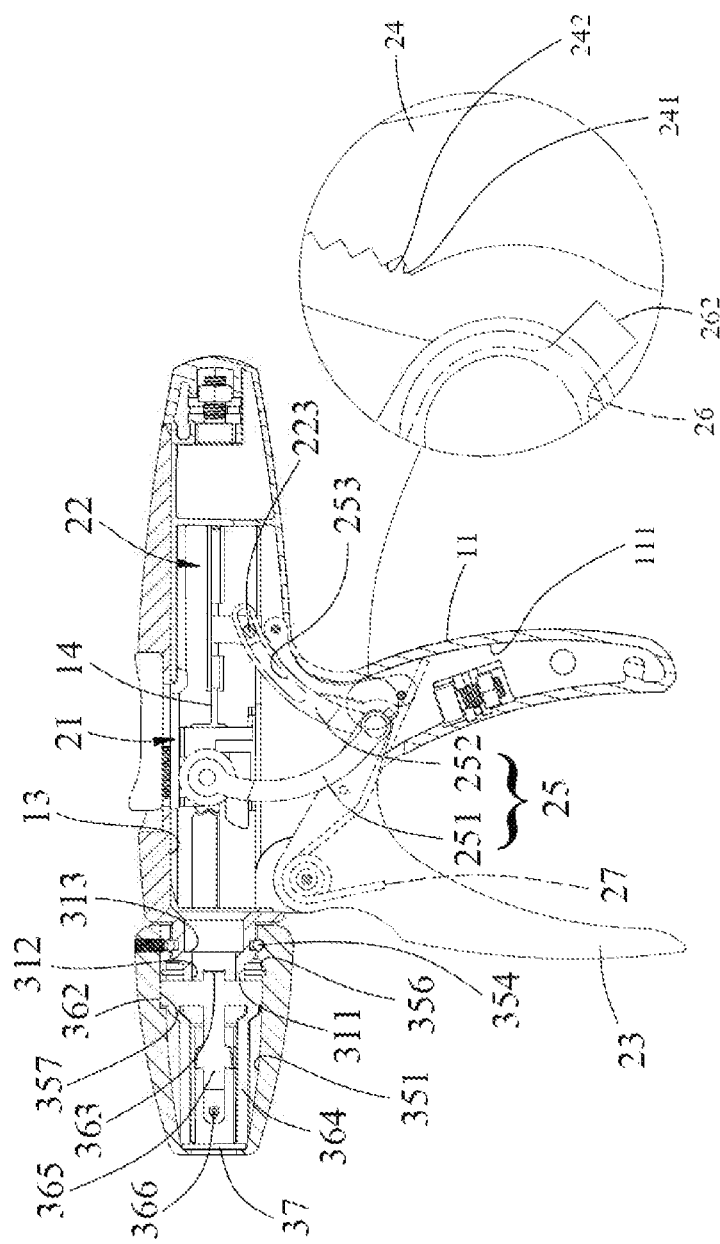
FIG. 5 is a cross-sectional view of a preferred embodiment of the present invention.

Now refer to FIG. 2, FIG. 3 and FIG. 5, the drive structure 20 includes a first slide block 21, a second slide block 22, a trigger 23, a ratchet gear 24, and a linkage assembly 25 disposed between the trigger 23, and the first slide block 21 and the second slide block 22. The first slide block 21 and the second slide block 22 are slidably disposed on the first track 13 and the second track 14, respectively. A first slide groove 211 is formed on the first slide block 21 and is opened at a top portion of the first slide block 21, the first slide block 21 has a portion protruding inwardly toward the first slide groove 211 forming a first connecting shape 212, the first connecting shape 212 is located at the center of the first slide groove 211. A second slide groove 221 is formed on the second slide block 22 and is opened at a top portion of the second slide block 22, the second slide block 22 has a portion protruding inwardly toward the second slide groove 221 forming a second connecting shape 222. The second connecting shape 222 is located at a front side of the second slide groove 221. A push rod 223 is laterally formed through a bottom part of the second slide groove 22. According to a preferred embodiment of the present invention, the push rod 223 may be a rivet. The ends of the push rod 223 are extended out of the second slide block 22.

A top portion of the trigger 23 is passed through the trigger opening 15, a front side of the top portion of the trigger 23 is located in the bottom side of the front end portion of the barrel part 12. A trigger shaft hole 231 is penetrated through the front side of the top portion of the trigger 23, which is aligned and communicated with the barrel part shaft hole 16. The top portion of the front side of the trigger 23 is pivotally connected to the bottom side of the front end portion of the barrel part 12. The detail of such pivoting structure will be specified later. The top portion of the trigger 23 extends rearward to form a drive aim 232, where the drive arm 232 includes two laterally symmetrical drive aim side plates 233. A spring rod 234 is disposed through the two drive arm side plates 233. A pivot rod 235 is penetrated through two respective free ends of the two drive arm side plates 233. According to a preferred embodiment of the present invention, the pivot rod 235 and the spring rod 234 are rivets.

A pawl piece 26 is pivotally formed on the pivot rod 235, a pawl spring 261 is disposed between a front end of the pawl piece 26 and the spring rod 234. A rear end of the pawl piece 26 has a pawl 262, the ratchet gear 24 is fixed within the accommodation space 111 inside the grip part 11, a front side of the ratchet gear 24 has numerous arc-shape arranged upward teeth 241, and each of the upward teeth 241 has a top end forming with a downward tooth 242. By operating the pawl 262 with either the upward teeth 241 or the downward teeth 242, the trigger 23 is only allowed to be moved in a single direction depending on whether it is being pulled rearward or returning frontward to its original position within the scope of the swing of the trigger 23. A return spring 27 is set between the trigger 23 and the inner side of the handle body 10, so that the trigger 23 can be returned to its original position by the releasing force provided by the return spring 27 when the trigger 23 is released after being pulled by the user. According to a preferred embodiment of the present invention, the return spring 27 is a torque spring.

The linkage assembly 25 includes two symmetrically disposed first linkages 251 and two symmetrically disposed second linkages 252. The bottom ends of the first linkages 251 are pivotally connected to the pivot arm 235 disposed at a free end of the drive arm 232. The top ends of the first linkages 251 are extended upwardly and frontward to be respectively connected to the sides of the first block 21, a pulley 2511 is concentrically connected to each of the pivots where the first linkages 251 and the first blocks 21 are pivotally connected. The pulleys 2511 are slidably disposed on the first track 13, the first slide block 21 can be sled more smoothly on the first track 13 by interoperating with the two pulleys 2511. Two respective bottom ends of the two second linkages 252 are pivotally connected to the pivot rod 235 disposed at the free end of the drive arm 232, two respective top ends of the two second linkages 252 are extended upwardly and rearward, each of the second linkages 252 has an upper portion with an arc-shaped slot 253 formed on. The end of the push rod 223 respectively passes through the arc-shaped slots 253. When the trigger 23 is being pulled and moved rearward, a first movement and a second movement may be performed respectively by the movements of the first slide block 21 and the second slide block 22, which are both moved by the linkage assembly 25.

The first movement is the movement of the first block 21 which is moved frontward along the first track 13 by the two first linkages 251 at the time the trigger 23 has been pulled rearward, and the second movement includes the movements of the two arc-shaped slots 253 being moved rearward causing the front edge of the two arc-shaped slot 253 being pushed against the push rod 223 at the time the trigger 23 has been pulled rearward, thereby driving the second block 22 to be moved rearward along the second track 14.

Figure 4:
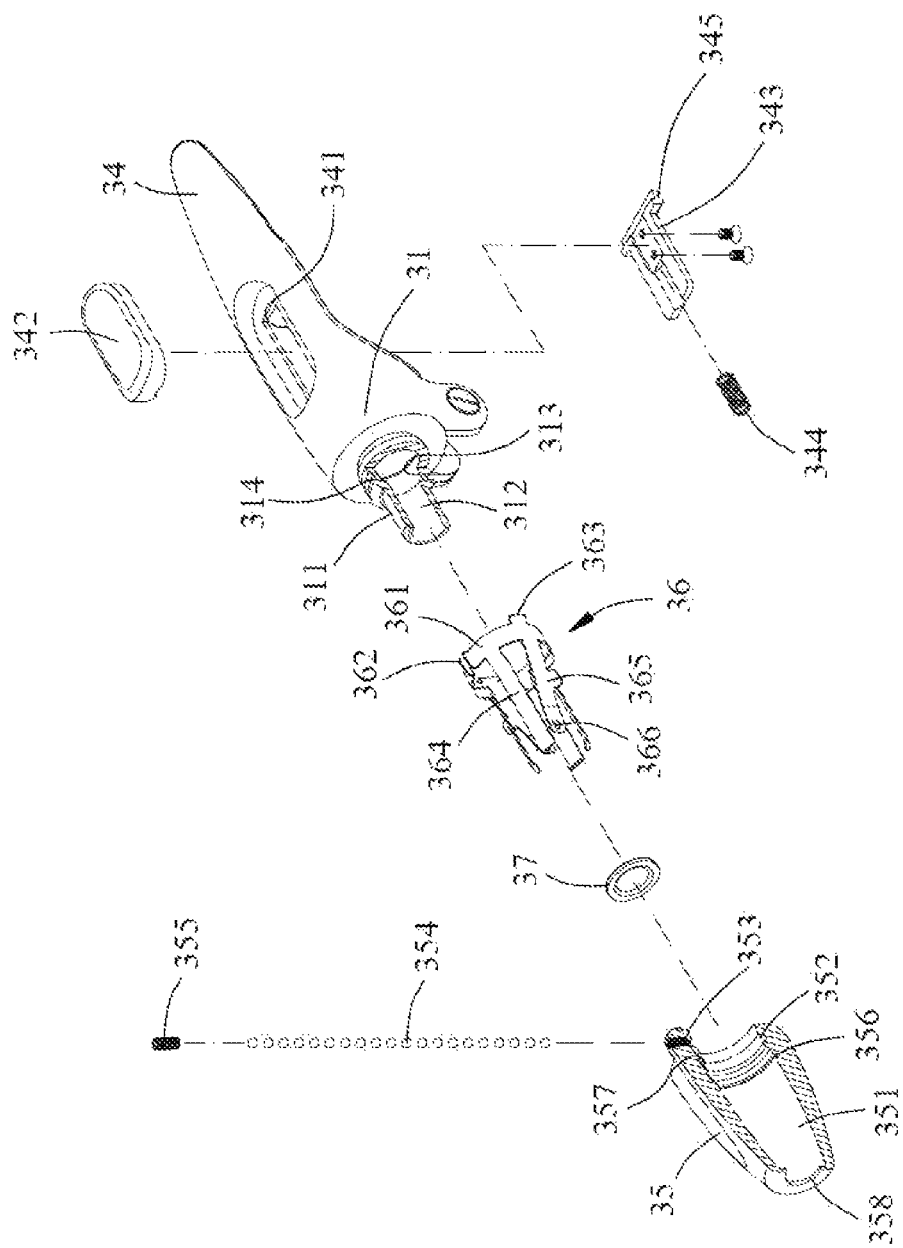
FIG. 4 is an explosion view illustrating the head unit according to an embodiment of the present invention.

With reference to FIG. 2 to FIG. 4, the head unit 30 has a head portion 31, the head portion 31 is a cover having an opening opened rearward and covering the front end portion of the barrel part 12, the center portion of the front side of the head portion 31 extends frontward to form a front tube 311. A front channel 312 is penetrated through the front tube 311 and the head portion 31. The rear end of the front channel 312 communicates with the track receiving space 121, the peripheral edge of the rear end of the front channel 312 is expanded radially to form a fixing portion 313. An outer ball groove 314 is formed around an outer periphery of the front tube 311. A pivot portion 32 is extended downwardly from the bottom side of the head portion 31, in which the pivot portion 32 includes two pivot arms 321 extended downwardly from the bottom side of the head portion 31, two pivot holes 322 are formed at two respective free ends of the two pivot arms 321. The pivot holes 322 are aligned and communicated with the barrel shaft hole 16. A front shaft 33 is disposed through the trigger shaft hole 231, the barrel shaft hole 16, and the pivot holes 322. According to a preferred embodiment of the present invention, the front shaft 33 can be a combination of a flat-head screw and a nut, and that the top end of the trigger 23 can be pivotally connected to the bottom side of the front end portion of the barrel part 12. The aforementioned return spring 27 is set around the front shaft 33 and has two ends respectively abutted with the trigger 23 and the inner side of the handle body 10.

The top side of the head portion 31 extends rearward to form an upper cover 34 for closing the embedding opening 122 located at the top portion of the barrel part 12. A switch piece opening 341 is a longitudinal slot formed on the upper cover 34, and a switch piece 342 is slidably embedded in the switch piece opening 341. A switch piece linking unit 343 is disposed on the bottom part of the switch piece 342, a switch piece spring 344 is abutted to a front edge of the switch piece opening 341 and the switch piece linking unit 343, a snap joint 345 is disposed at each side of the switch piece linking unit 343 corresponding to the aperture 123 of the barrel part 12, the snap joint 345 is connected to a rear edge of a bottom edge of the aperture 123. The aforementioned structure is the switch structure for fixing the head unit 30 to the barrel part 12. A bottom side of the switch piece linking unit 343 has a suppressing portion 346 formed in an arc shape.

A rotation wheel 35 is disposed around the front tube 311. The rotation wheel 35 is in a barrel shape and has a rotation wheel channel 351 penetrating through the center and along the axial direction of the rotation wheel 35. The front tube 311 is at least partially located in a rear part of the rotation wheel channel 351, a circumferential wall of the rear part of the rotation wheel channel 351 has an inner ball groove 352 corresponding to the outer ball groove 314, a ball receiving hole 353 is formed between the outer periphery of the rotation wheel 35 and the inner ball groove 352, a number of balls 354 are disposed inside the outer ball groove 314 and the inner ball groove 352. A part of each of the balls 354 is located in the inner ball groove 352, whereas the other part of each of the balls 354 is located in the outer ball groove 314, and the ball receiving hole 353 is assembled with a closure 355. According to a preferred embodiment of the present invention, the ball receiving hole 353 is a screw hole and the closure 355 is a screw. A connecting groove 356 is formed around the circumferential wall of the rotation wheel channel 351, and a side of the circumferential wall of the rotation wheel channel 351 has a key slot 357 formed along a direction from the front to the rear, the rear end of the key slot 357 is penetrated through the peripheral edge of the rear end of the rotation wheel channel 351, a front flange 358 is formed inwardly from the peripheral edge of the front end of the rotation wheel channel 351.

An elastic piece assembly 36 is embedded inside the rotation wheel channel 351, a ring piece 361 of the elastic piece assembly 36 is abutted with the circumferential wall of the rotation wheel channel 351 and is formed in a C shape having two respective key pieces 362 at the two free ends, the two key pieces 362 are plugged into the key slot 357 for positioning, an outer periphery of the ring piece 361 has a plurality of connecting plates 363 formed outwardly, the connecting plates 363 are positioned into the connecting groove 356, the ring piece 361 has a number of abutting pieces 364 circumferentially formed at intervals and being long-strip pieces extended toward the front. An oil seal ring 37 is positioned between the front ends of the abutting pieces 364 and the front flange 358, two positioning plates 365 are formed frontward from the ring piece 361, and two fixing points 366 are formed on each of two respective free ends of the positioning plates 365, respectively Referring to FIG. 6, while operating the present invention according to a preferred embodiment, a conventional clamping assembly 40 can be used. The clamping assembly 40 has an outer sheath 41, and the front end of the clamping assembly 40 has a clamping portion 42. The clamping portion 42 has a vessel clip 43 that can be moved frontward in the clamping assembly 40. Each lateral side of the rear end of the outer sheath 41 has a positioning hole 45, and the periphery of the rear end of the outer sheath 41 has a positioning ring 46 protruded outwardly. The front part and rear part of the rear portion of the clamping assembly 40 which are not covered by the outer sheath 41 are respectively sleeved with a first sleeve 47 and a second sleeve 48. A first groove 471 is formed around the first sleeve 47, and a second groove 481 is formed around the second sleeve 48.

The clamping portion 42 can perform clamping movements by moving the first sleeve 47 frontward; at the beginning of a frontward movement of the first sleeve 47, the second sleeve 48 will be moved toward the front together with the first sleeve 47. Then, while the second sleeve 48 reaches a later position, it will no longer be moved together with the first sleeve 47. At that time the second sleeve 48 can be driven to move rearward. By operating with this movement, i.e. the frontward and rearward movement of the second sleeve 48, the vessel clip 43 can be brought frontward to the inner side of the clamping portion 42 to be ready for clipping. A return unit 49 is disposed at the rear end of the clamping assembly 40 for returning the first sleeve 47 and the second sleeve 48 back to their original positions.

Figure 6:
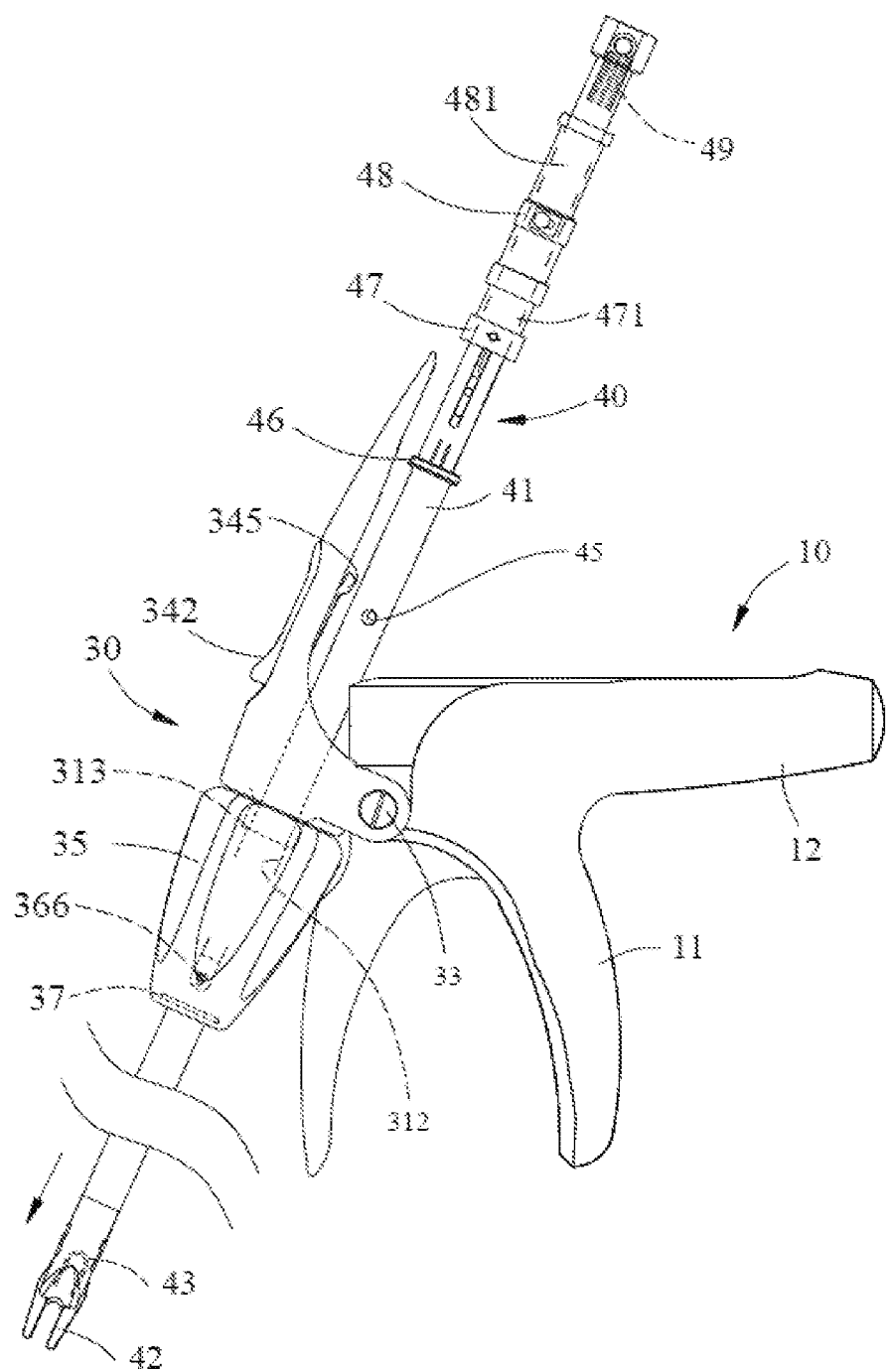
FIG. 6 is a schematic view illustrating the operation of installing a clamping assembly according to a preferred embodiment of the present invention.

While operating the present invention with the clamping assembly 40, as shown in FIG. 2 and FIG. 6, the switch piece 342 of the head unit 30 will be pushed frontward, the snap joint 345 of the bottom portion of the switch piece 342 will be moved frontward to the position where the aperture 123 is located. Then, the head unit 30 will be flipped frontward around the front shaft 33, and the upper cover 34 will be moved away from the embedding opening 122, thereby keeping the embedding opening 122 in an open status.

Next, while having the grip part 11 of the handle body 10 in one hand of the user, and the other hand holding the clamping assembly 40, the front end of the clamping assembly 40 can be pointed downwardly and inserted into the front channel 312 and the oil seal ring 37 of the head unit 30 until the positioning ring 46 of the clamping assembly 40 has reached the fixing portion 313 inside the head unit 30. Meanwhile, the fixing points 366 will be snapped into the positioning holes 45 for positioning, so that the rotation of the rotation wheel 35 can be linked to the adjustment of the install angle of the clamping assembly 40.

While the clamping assembly 40 has been inserted through the front channel 312 of the head unit 30 and positioned, the head unit 30 can be flipped rearward by the user to cover the upper cover 34 over the embedding opening 122, and the snap joint 345 of the bottom part of the switch piece 342 can be reconnected with the bottom edge of the rear side of the aperture 123 in order to fix the relative position of the head unit 30 and the handle body 10. Additionally, when flipping the head unit 30 rearward, the rear end of the clamping assembly 40 will be inserted downwardly from the embedding opening 122 at the top portion of the barrel part 12 into the barrel part 12, so that the first sleeve 47 of the clamping assembly 40 can be embedded into the first slide block 21, and the second sleeve 48 can be embedded into the second slide block 22, where the first connecting shape 212 can be fitted with the first groove 471, and the second connecting shape 222 can be fitted into the front side of the second groove 481.

Figure 7:
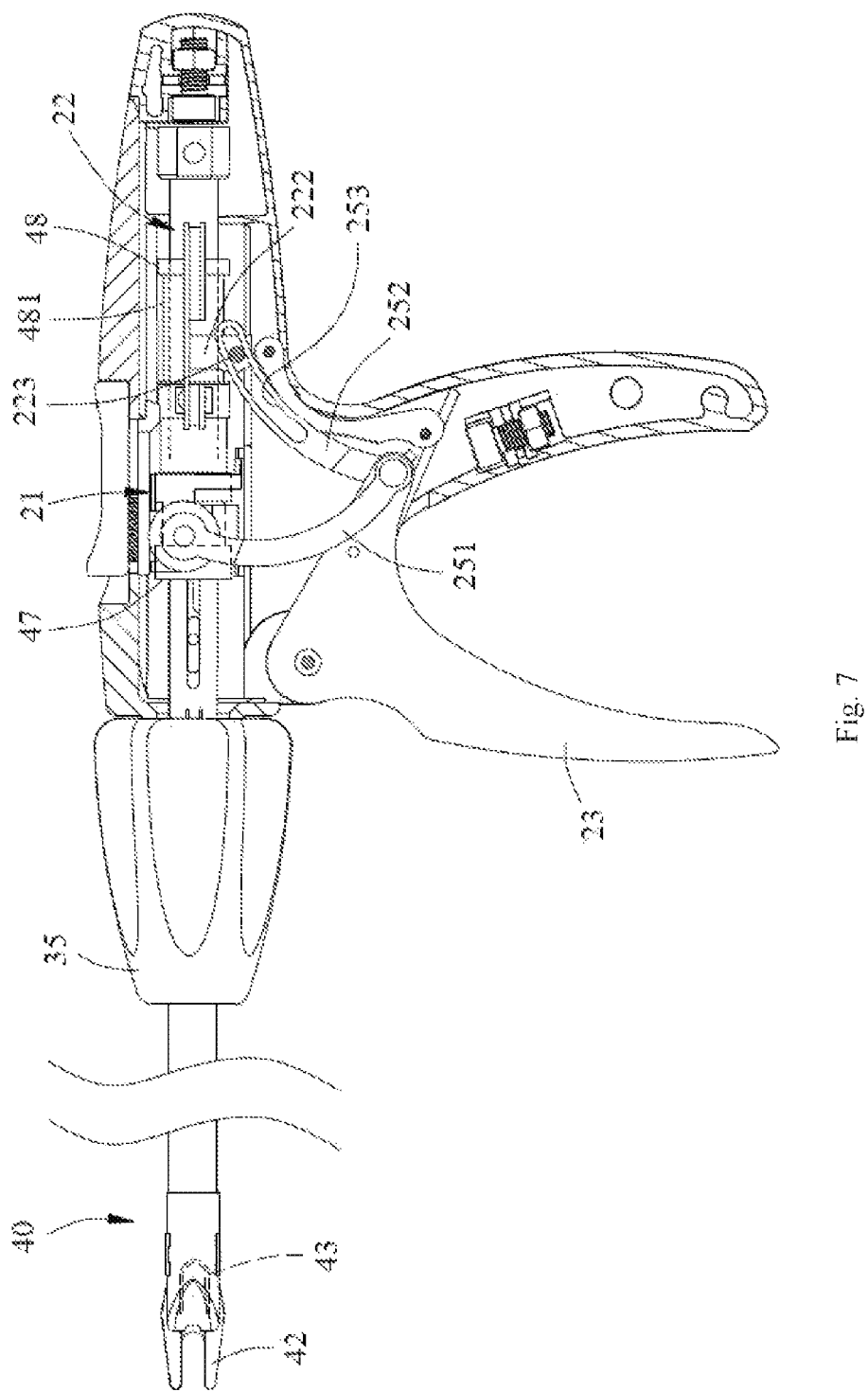
FIG. 7 is a partial cross-sectional diagram illustrating the installation of the clamping assembly according to a preferred embodiment of the present invention.
Figure 8:
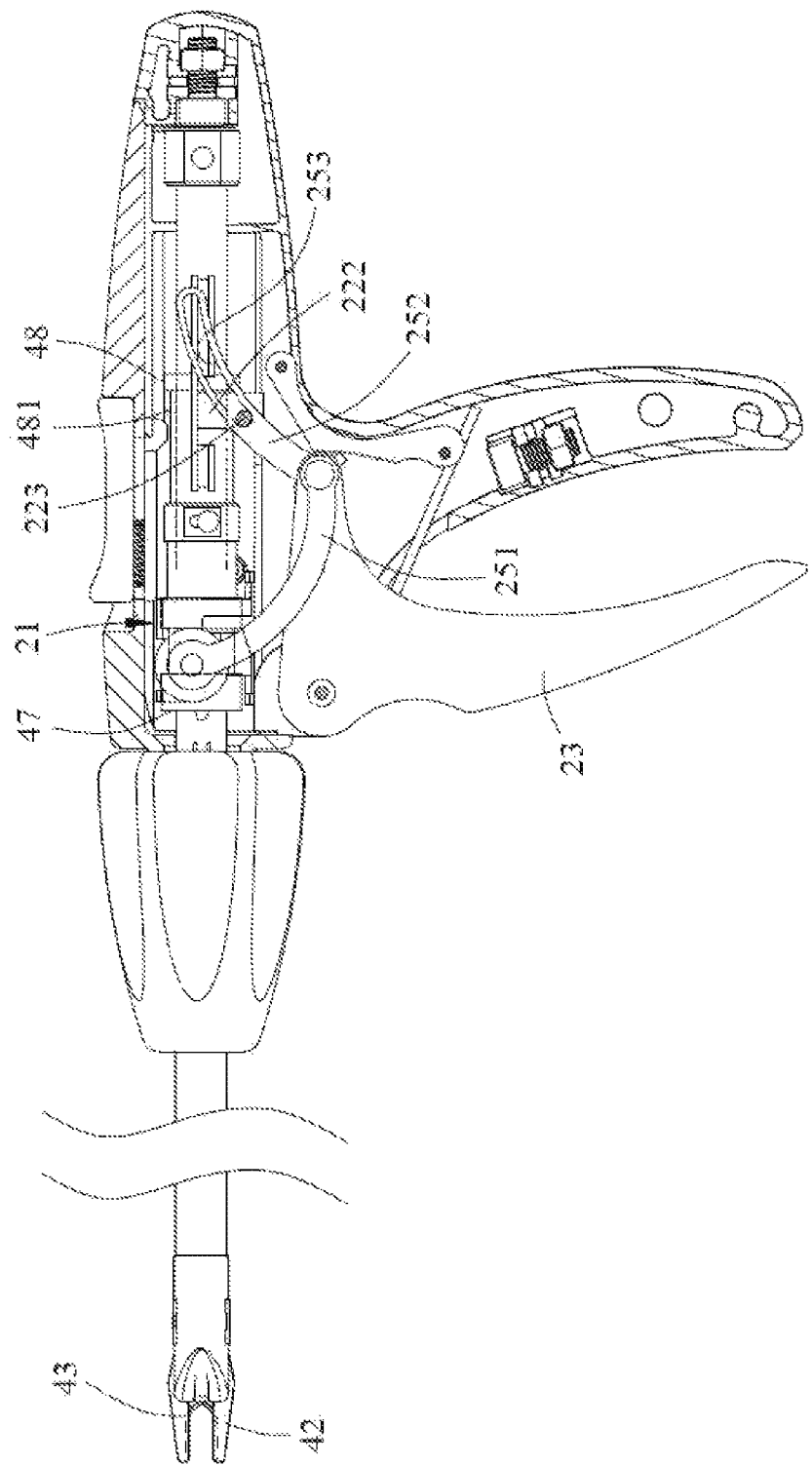
FIG. 8 is a schematic view illustrating the operation of the clamping assembly according to a preferred embodiment of the present invention.

The process of the vessel clip 43 being clamped by the clamping portion 42 at the front end of the clamping assembly 40 of the present invention is performed by pulling the trigger 23 rearward by the hand gripping the grip part 11 of the user. Refer to FIG. 7 and FIG. 8 illustrating the trigger 23 pulling process, the first linkage 251 will drive the first slide block 21 and the first sleeve 47 to be moving frontward, and while the second linkage 252 moves, the arc-shaped slot 253 of the second linkage 252 will be moved rearward along the push rod 223. While the first sleeve 47 moves frontward, it drives the second sleeve 48 to be moving frontward, so that the second sleeve 48 will move frontward and the rear edge of the second groove 481 will be abutted against the second connecting shape 222.

Figure 9:
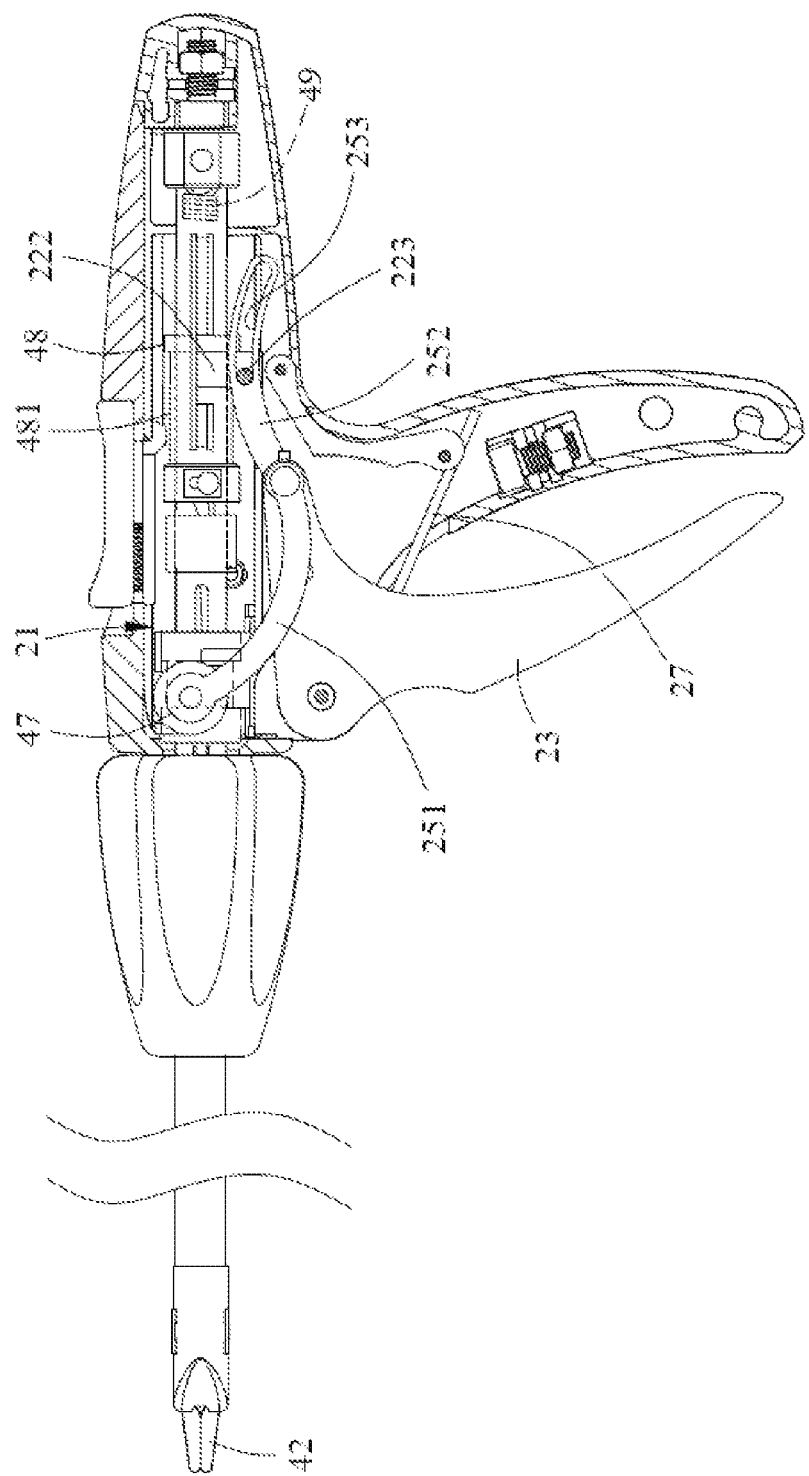
FIG. 9 is a schematic view illustrating the operation of the clamping assembly according to a preferred embodiment of the present invention.

As shown in FIG. 8, when the rear edge of the second groove 481 is abutted against the second connecting shape 222, the front edge of the arc-shaped slot 253 of the second linkage 252 will also be reaching the push rod 223. At this moment, the second sleeve 48 will no longer be moved with the first sleeve 47, referring to FIG. 9, while the trigger 23 is continued to be pulled further, the front edge of the arc-shaped slot 253 will push the push rod 223 as well as the second sleeve 48 to be moving rearward.

By performing the aforementioned movement of pulling the trigger 23, the first sleeve 47 of the clamping assembly 40 will be moved frontward, and the second sleeve 48 will be moved frontward at the beginning and then rearwards, the vessel clip 43 being sent frontward can be clamped by the clamping portion 42 of the clamping assembly 40. When the trigger 23 is released, the trigger 23 can be returned to the original position not only by the return spring 27, but the rearward movement of the first sleeve 47 that drives the first linkage 251 back to its original position.

While the operation of the clamping assembly 40 is finished, where the clamping assembly 40 is to be removed, the switch piece 342 can be pushed frontward in order to flip up the head unit 30, referring to FIG. 6, then, the clamping assembly 40 can be pulled out upwardly from the head unit 30. During this process, the blood and body fluids around the clamping assembly 40 can also be scraped off by the oil seal ring 37 of the front end of the rotation wheel 35. Because the clamping assemblies 40 can be repeatedly installed with and removed from the surgical vessel clip applier handle of the present invention, the surgical vessel clip applier handle can be reused after sterilization before performing each surgical operation instead of being disposed after each time being used, thereby being more economically efficient. The risk of infection can be remained low as well by using new clamping assemblies 40 while performing surgical operations.

The switch structure used for positioning the head unit 30 and the barrel part 12 set forth above where the switch piece 342 is disposed at the upper cover 34 is only for exemplary purpose, in other embodiments, the switch piece 342 may also be disposed at the top portion of the barrel part 12 for joining the edge of the upper cover 34 in order to fix the relative positions of the head unit 30 and the barrel part 12. Besides, the head portion 31 of the head unit 30 can not only be a cover covering the front end portion of the barrel part 12 as mentioned above, it can also be a block located at the front end portion of the barrel part 12.

The description of the invention including its applications and advantages as set forth herein is illustrative and is not intended to limit the scope of the invention, which is set forth in the claims Variations and modifications of the embodiments disclosed herein are possible, and practical alternatives to and equivalents of the various elements of the embodiments would be understood to those of ordinary skill in the art upon study of this patent document. For example, specific values given herein are illustrative unless identified as being otherwise, and may be varied as a matter of design consideration. Terms such as "target" and "background" or so are distinguishing terms and are not to be construed to imply an order or a specific part of the whole. These and other variations and modifications of the embodiments disclosed herein, including of the alternatives and equivalents of the various elements of the embodiments, may be made without departing from the scope and spirit of the invention, including the invention as set forth in the following claims.

What is claimed is:

1. A surgical vessel clip applier handle, comprising:
   a handle body, being a shell and comprising a grip part and a barrel part, wherein a top portion of the grip part is connected to a bottom side of a front end portion of the barrel part, a track receiving space is formed inside the barrel part and extends along an axial direction of the barrel part, a top side of the barrel part has an embedding opening formed along the barrel part, a front end of the track receiving space and a front end of the embedding opening are open ends, a first track and a second track are respectively formed at a front portion and a rear portion of the track receiving space inside the barrel part, both the first track and the second track are tracks extending along the axial direction of the barrel part, a trigger opening is formed at the junction of where a front end of the top portion of the grip part and the bottom side of the barrel part are connected;
   a drive structure, having a first slide block and a second slide block slidably disposed on the first track and the second track, respectively, and a first slide groove and a second slide groove respectively formed on the first slide block and the second slide block, wherein the first slide groove is opened at a top portion of the first slide block, and the second slide groove is opened at a top portion of the second slide block, the first slide block has a portion protruding inwardly toward the first slide groove forming a first connecting shape, the second slide block has a portion protruding inwardly toward the second slide groove forming a second connecting shape; wherein the drive structure has a trigger, a top portion of the trigger is passed through the trigger opening, the top portion of the trigger is pivotally connected to the front end of the bottom side of the barrel part, a drive arm is formed on and extended rearward from the trigger, a linkage assembly is disposed between a free end of the trigger, and the first slide block and the second slide block, thereby a first movement and a second movement of the first slide block and the second slide block are performed while the trigger has been pulled rearward to move the first slide block and the second slide block through the linkage assembly; and
   a head unit, having a head portion located at the front end portion of the barrel part, and a front tube extended from a center portion of the head portion toward the front, wherein a front channel is formed inside the front tube and the head portion, the front channel is communicated with the track receiving space, the periphery of the rear end of the front channel is expanded radially to form a fixing portion, a bottom side of the head portion has a pivot portion extended downwardly therefrom for pivotally connecting to the front end of the bottom side of the barrel part, a top side of the head portion is extended rearward to form an upper cover for closing the embedding opening, a switch structure is disposed between the periphery of the embedding opening and the upper cover.

2. The surgical vessel clip applier handle as claimed in claim 1, wherein a return spring is abutted between the trigger and the inner side of the handle body, and a rotation wheel is disposed around the front tube, an oil seal ring is disposed inside the rotation wheel, two elastic clipping points are disposed oppositely at a side of the oil seal ring.

3. The surgical vessel clip applier handle as claimed in claim 2, wherein an outer ball groove is formed around the outer periphery of the front tube, the rotation wheel is in a barrel shape and has a rotation wheel channel penetrated through the center and along the axial direction thereof, the front tube is at least partially located in a rear part of the rotation wheel channel, a circumferential wall of the rear part of the rotation wheel channel has an inner ball groove corresponding to the outer ball groove, a ball receiving hole is formed between an outer periphery of the rotation wheel and the inner ball groove, a plurality of balls are disposed inside the outer ball groove and the inner ball groove, wherein a part of each of the balls is located in the inner ball groove, the other part of each of the balls is located in the outer ball groove, and the ball receiving hole is assembled with a closure.

4. The surgical vessel clip applier handle as claimed in claim 3, wherein a connecting groove is formed around the circumferential wall of the rotation wheel channel, and a side of the circumferential wall of the rotation wheel channel has a key slot formed along a direction from the front to the rear, a rear end of the key slot is penetrated through the peripheral edge of the rear end of the rotation wheel channel, a front flange is formed inwardly from a peripheral edge of the front end of the rotation wheel channel, an elastic piece assembly is embedded inside the rotation wheel channel, a ring piece of the elastic piece assembly is abutted with the circumferential wall of the rotation wheel channel and is formed in a C shape having two respective key pieces at two free ends thereof, the two key pieces are plugged into the key slot for positioning, an outer periphery of the ring piece has a plurality of connecting plates formed outwardly, each of the connecting plates are positioned into the connecting groove, the ring piece has a plurality of abut pieces circumferentially formed at intervals and extended toward the front, the oil seal ring is positioned between a front ends of the abut pieces and the front flange, two positioning plates are formed frontward from the ring piece, and two fixing points are formed on a free end of each of the two positioning plates, respectively.

5. The surgical vessel clip applier handle as claimed in claim 1, wherein the linkage assembly comprises two symmetrically disposed first linkages and two symmetrically disposed second linkages, each of the first linkages has a bottom end pivotally connected to a free end of the drive arm, each of the first linkages has a top end extended upwardly and frontward to be pivotally connected to the both sides of the first block, respectively, the bottom part of the second block has a push rod laterally penetrated therethrough, each of the second linkages has a bottom end pivotally connected to the free end of the drive arm, the top ends of the second linkages are extended upwardly and rearward, each of the second linkages has an upper part having an arc-shaped slot formed thereon, the push rod is disposed through the two arc-shaped slots, the first movement is the movement of the first block being moved frontward along the first track by the two first linkages at the time the trigger has been pulled rearward, and the second movement includes the movements of the two arc-shaped slot being moved rearward along the push rod causing two respective front edges of the two arc-shaped slot being pushed against the push rod at the time the trigger has been pulled rearward, thereby driving the second block to be moved rearward along the second track.

6. The surgical vessel clip applier handle as claimed in claim 5, wherein the upper cover of the switch structure has a switch piece, a bottom part of the switch piece has a snap joint connected with a peripheral edge of the embedding opening.

7. The surgical vessel clip applier handle as claimed in claim 6, wherein a switch piece opening is formed on the upper cover, the switch piece is slidably embedded in the switch piece opening, the bottom part of the switch piece has a switch piece linking unit, a switch piece spring is abutted to a front edge of the switch piece opening and the switch piece linking unit, the snap joint is disposed at both sides of the switch piece linking unit, an aperture is formed at the opposite sides of the peripheral edge of the embedding opening and is corresponded to the snap joint, the snap joint is connected to the rear edge of the bottom edge of the aperture, a bottom side of the switch piece linking unit has a suppressing portion formed in an arc shape.

8. The surgical vessel clip applier handle as claimed in claim 7, wherein the trigger opening is extended frontward to the bottom side of the front edge of the barrel part, a barrel part shaft hole is formed laterally at the front edge of the bottom part of the barrel part and penetrated therethrough, the top end of the front side of the trigger has a trigger shaft hole communicating with the barrel shaft hole, the head portion of the head unit is a cover covering the front end portion of the barrel part, the pivot portion comprises two pivot arms extended symmetrically and downwardly from two lateral sides of the bottom part of the head portion, each of the pivot arms has a free end having a pivot hole communicating with the barrel part shaft hole, wherein a front shaft is disposed through the trigger shaft hole, the barrel part shaft hole and the pivot hole.

9. The surgical vessel clip applier handle as claimed in claim 8, wherein the drive arm comprises two laterally symmetrical drive arm side plates having a spring rod penetrated therethrough, each of the two drive arm side plates has a free end having a trigger shaft penetrated therethrough, a pawl piece is sleeved on the trigger shaft, a pawl spring is connected between a front end of the pawl piece and the spring rod, a rear end of the pawl piece is formed into a pawl, a ratchet gear corresponding to the pawl is fixed in the grip part, a front side of the ratchet gear has a plurality of upward teeth arranged in an arc shape, and each of the upward teeth has a top end of formed with a downward tooth.

10. The surgical vessel clip applier handle as claimed in claim 9, wherein the trigger shaft is penetrated through the bottom ends of the first linkages and the bottom ends of the second linkages, thereby pivotally connecting the bottom ends of the first linkages and the bottom ends of the second linkages to the free end of the drive arm.

\* \* \* \* \*